Figure 1:
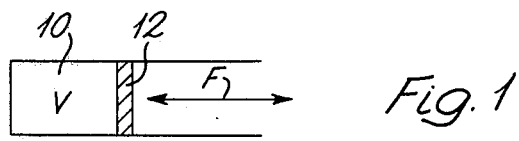

United States Patent [19]

Froome

[11] 4,327,585
[45] May 4, 1982

[54] REFRACTOMETER

[75] Inventor: Keith D. Froome, Hampton, England

[73] Assignee: National Research Development Corporation, London, England

[21] Appl. No.: 149,559

[22] Filed: May 13, 1980

[30] Foreign Application Priority Data

May 31, 1979 [GB] United Kingdom ............... 7918960

[51] Int. Cl.³ ..................... G01D 21/02; G01N 21/41
[52] U.S. Cl. ...................................... 374/45; 73/386; 356/128; 374/143
[58] Field of Search ................. 73/384, 386, 701, 708, 73/345; 356/128; 324/58 B

[56] References Cited

U.S. PATENT DOCUMENTS 1,690,455 11/1928 Pawlin ................................ 73/386
2,270,494 1/1942 Barnhart ............................ 73/345
2,957,350 10/1960 Kolb .................................. 73/726
3,439,356 4/1969 Kinzer ............................... 73/345

FOREIGN PATENT DOCUMENTS 1425745 2/1976 United Kingdom ............... 73/345

Primary Examiner—James J. Gill
Attorney, Agent, or Firm—Cushman, Darby & Cushman

[57] ABSTRACT

A terrestrial refractometer comprises a gastight enclosure containing a fixed mass of a gas which at least approximates to an ideal gas, at least a part of the enclosure being movable in response to changes in the volume of the gas in accordance with changes in ambient temperature and pressure; constraining means for constraining said movable part so as to maintain the gas at a constant volume; and sensing means for providing a signal related to the force applied to the movable part by the constraining means.

6 Claims, 5 Drawing Figures

REFRACTOMETER

This invention relates to refractometers, that is, devices which can provide a signal relating to refractive index.

It may be a requirement of physical measurements over long distances on the earth's surface, such as, for example, electromagnetic distance measurements at optical wavelengths, that an accurate measure is available of the refractive index of the terrestrial atmosphere through which the measurement is made. In one method this is obtained by separate measurements of temperature and pressure; corrections for refractivity are then made by reference to tables or use of a special slide rule. In another method, as described in the specification of UK Pat. No. 1425745, an automatic correction is applied by using the properties of a fixed mass of ideal gas constrained in a flexible bellows, the expansion and contraction of the bellows varying with ambient temperature and pressure, and the movement being used to provide a correction factor. However, the described method and apparatus may not provide a completely accurate correction factor, because the inherent springiness or stiffness of the bellows resists both expansion and contraction.

The present invention relates to an improved device which can provide a signal related to the refractive index under ambient conditions of temperature and pressure of the air near the surface of the earth, and the device will therefore be referred to as a terrestrial refractometer.

According to the invention a terrestrial refractometer comprises a gastight enclosure containing a fixed mass of a dry gas which at least approximates to an ideal gas, at least a part of the enclosure being movable in response to changes in the volume of the gas in accordance with changes in ambient temperature and pressure; constraining means for constraining said movable part so as to maintain the gas at a constant volume; and sensing means for providing a signal related to the force applied to the movable part by the constraining means.

It will be shown below that the constraining force varies with temperature and pressure in a manner related to the refractive index of the earth's atmosphere.

Preferably the movable part is movable only linearly, with substantially no component of movement in the transverse direction, in which case the required force can be applied by simple mechanical means such as a helical spring, or by an electrical force sensor or strain gauge.

In one embodiment the refractometer comprises a closed gastight container of substantially invariant transverse section and having a first endwall fixed in position and a second, opposite endwall which varies in distance from the first endwall in accordance with ambient temperature and pressure, unless constrained. Conveniently the container is the metal bellows of an aneroid barometer.

Also according to the invention, a method of providing a measure of the refractive index of the earth's atmosphere comprises exposing to ambient pressure and temperature a gastight enclosure containing a fixed mass of a dry gas which at least approximates to an ideal gas, at least a part of the enclosure being movable in response to changes in the volume of the gas; constraining said movable part so as to maintain the gas at constant volume; and sensing the force required to provide the constraint.

Figure 2:
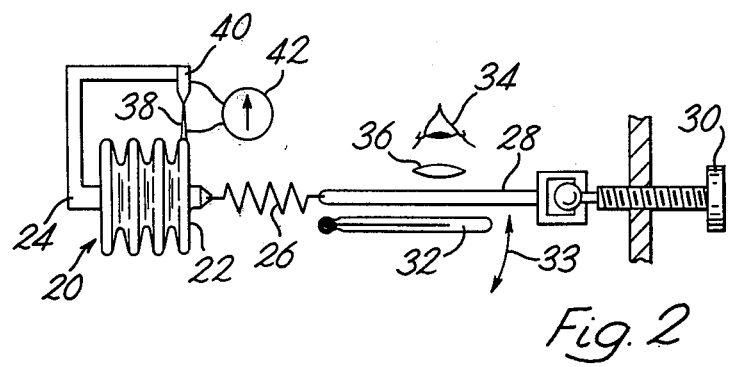
Figure 3:
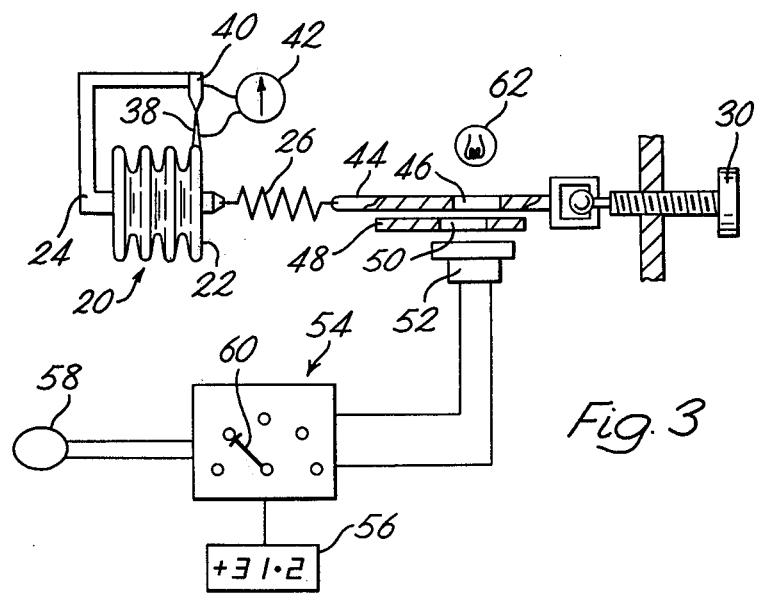
Figure 4:
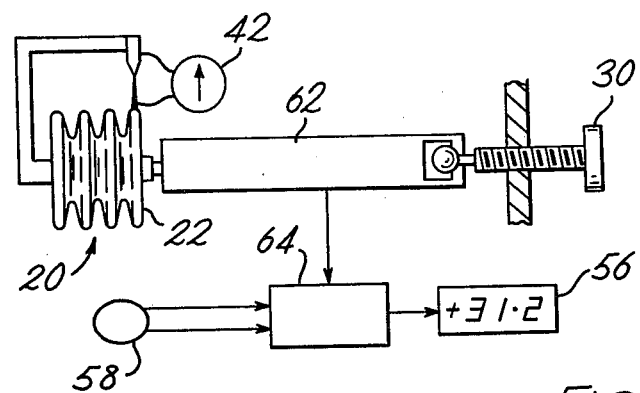
Figure 5:
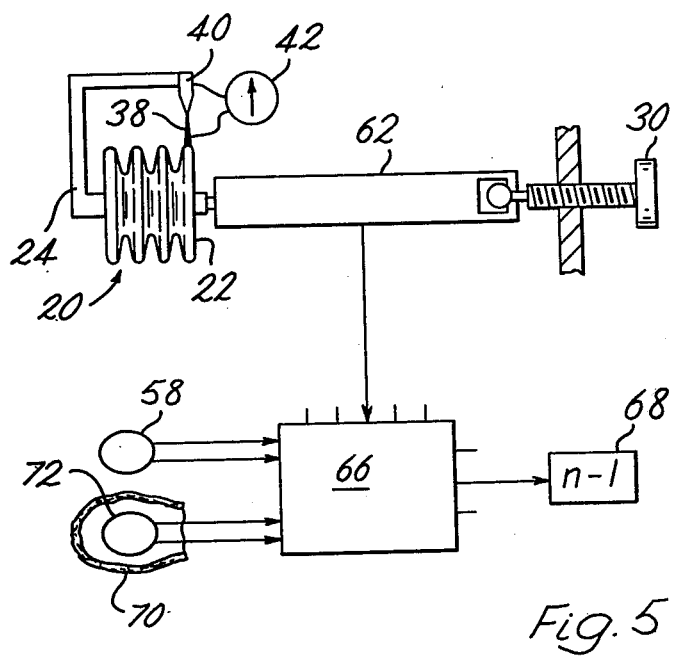

The invention will now be described with reference to the accompanying drawings in which:

FIG. 1 indicates the principle of the invention;

FIGS. 2, 3 and 4 illustrate three optical refractometers according to the invention having different force-sensing systems; and FIG. 5 illustrates a refractometer for microwave radiation.

First, consider the refractive index of the earth's atmosphere at sea level; the value changes by about 1 part per million when there is a pressure change of 2.7 millimeters of mercury (3 millibars) or a temperature change of 1° C. Let the refractive index under standard temperature and pressure (0° C. or 15° C. and 1013 millibars, 760 millimeters Hg) be $n_o$ and under ambient conditions be n. Then:

$$(n - 1) = (n_o - 1)\frac{P}{P_o} \cdot \frac{T_o}{T} \quad [1]$$

Thus $$dn = (n_o - 1) - (n - 1) = (n_o - 1)\left[1 - \frac{P}{P_o} \cdot \frac{T_o}{T}\right] \quad [2]$$

Referring now to FIG. 1, a rigid cylinder 10 contains a fixed mass of an ideal gas, such as dry air, constrained by a piston 12. If the volume of the gas is V at standard temperature and pressure, from the gas laws:

$$P_o = RT_o/V$$

and at temperature T:

$$P_T = RT/V$$

Therefore at constant V:

$$P_T = P_o T/T_o$$

If the ambient atmospheric pressure is P, the force actually required to maintain the enclosure at volume V is:

$$P_T - P = dP$$

Thus $dP = P_o T/T_o - P$ or $P = P_o T/T_o - dP$ \quad [3]

Substituting for P in equation [1]

$$dn = (n_o - 1)\frac{dP}{P_o} \cdot \frac{T_o}{T}$$

If T is expressed as t°C., then:

$$dn = (n_o - 1)\frac{dP}{P_o}\left[\frac{1}{1 + t/T_o}\right] \quad [4]$$

Since $n_o$, $P_o$ and $T_o$ are constant, it can be seen that dn is proportional to dP. While ambient temperature t°C. must be known, the temperature factor is reduced in comparison with that in equation [2] by a factor of dP, thus temperature need not be measured accurately.

It is to be understood that the equations given above hold at sea level and at heights up to ten (or more) thousand feet; that is, the refractometer according to the invention is essentially a terrestrial instrument.

Further, it is well known that the value of $n_o$ is a function of the wavelength at which it is measured, but is insensitive to atmospheric water vapour pressure, which therefore need not be considered.

FIG. 2 shows the first embodiment of the invention. A metal bellows 20, such as the bellows of an aneroid barometer, is fixed at one end to an insulating support 24 while the opposite end 22 is free to move linearly as the bellows expands and contracts. A helical spring 26 applies a force to the movable end 22 in the direction of movement. The opposite end of the spring is fixed to a transparent scale 28 which can be moved in the same linear direction as the bellows by an adjusting knob 30. Below the scale 28 is a simple mercury-in-glass thermometer 32 which can be viewed from position 34 through a lens 36.

Attached to the movable end 22 of the bellows is an electrical contact 38; a second contact 40 is carried by the insulating support 24 in a position which is fixed with respect to the fixed end of the bellows. An electrical meter 42 is connected between the contacts 38, 40.

In use, the bellows is exposed to ambient temperature and pressure, the adjusting knob 30 is rotated to apply pressure through the linear scale 28 to the helical spring which acts on the movable end 22 of the bellows. Adjustment is made until the meter 42 indicates that an electrical connection has been made between contacts 38 and 40. The volume of gas within the bellows is then the constant value V. The scale 28 is read through the lens 34, using the meniscus of mercury in the thermometer 32 as a reference point to provide adequate temperature compensation. Means (not shown) is provided for tilting the thermometer 32 in the plane of the drawing, as indicated by the arrow 33, so that as the adjusting knob 30 is altered, the magnitude of the temperature correction can be varied with dP, in accordance with equation [4]. The scale reading indicates the force applied to maintain the gas at volume V, and equation [4] can be applied to calculate dn.

Since the refractivity of air varies with wavelength, the scale 28 can be calibrated for light of several different colours, the appropriate scale being read each time. The thermometer 32 can be laterally movable to lie under the required scale.

Although in the illustration the helical spring must be compressed to restore the gas to volume V, it is also possible to use the spring under tension to expand the bellows to volume V.

In FIG. 3, the bellows 20, helical spring 26, adjusting knob 30 and electrical meter 42 are identical to those in FIG. 2, but the end of the spring is now attached to a plate 44 having in it a slit 46 the aperture of which varies as the force on the helical spring 26 varies. Below the plate 44 is a fixed plate 48 having a slit 50 of fixed aperture, and below both slits is a photodiode 52 connected to an electronic unit 54. The unit 54 has a digital display 56 and is connected to a thermistor 58 which provides adequate temperature compensation. The unit has a scale selector switch 60 by which the circuit can be varied so as to display change in refractive index at a selected wavelength. The photodiode 52 is illuminated through the slits 46, 50 by a light emitting diode 62.

As in the previous embodiment, adjusting knob 30 is rotated until the gas in the bellows is at volume V; the aperture of slit 46 varies accordingly, the intensity of light from the LED 62 reaching the photodiode 52 varies, and the electronic circuitry in effect applies equation [4] and provides a digital readout of either absolute refractive index at the selected wavelength, or change of refractive index from its value at standard temperature and pressure.

In the third embodiment, the helical spring 26 is replaced by a strain gauge 62 which is connected mechanically between the end 22 of the bellows and the adjusting knob 30, and is connected electrically to an electronic unit 64 which in turn is connected to a thermistor 58 and digital display 56. In this arrangement the strain gauge both applies the force to the movable end of the bellows, and supplies a signal related to that force to the unit 64 which controls the digital display as before.

The three practical embodiments described are merely examples, the principle of the invention can be applied in other ways.

The refractometers described above provide a measure of the variation from a standard condition of the refractivity of the earth's atmosphere at optical wavelengths. The present invention may also be applied to determine the microwave refractive index. FIG. 5 shows a variation of the apparatus in FIG. 4; the strain gauge 62 supplies its output signal to a microprocessor 66 which has a display unit 68 and which is connected to a thermistor 58 and to an identical thermistor 72 which is surrounded by an absorbent material 70 wetted with distilled water; the two thermistors will be referred to as the wet and dry thermistors providing values of temperature T and Tw.

It has been shown by Essen, C., and Froome, K.D., Proc. Phys. Soc. B 64, 862, 1951 "The Refractive Index of Air for Radio Waves and Microwaves," Pub. No. 65496 of The National Physical Laboratory, Teddington, that for microwaves travelling through the earth's atmosphere:

$$(n_t P - 1)10^6 = \frac{77.620P}{T} - \frac{12.91}{T}\left(1 - \frac{5748}{T}\right)P_w \quad [5]$$

where n is refractive index at temperature t°C. and P millibars, where $P_w$ is water vapour pressure in millibars. From equation [3]:

$$P/T = P_o/T_0 - dP/T$$

Thus the value of dP provided by the strain gauge 62 can be applied to equation 5 by the microprocessor 66. The value of $P_w$ is provided by the wet and dry thermistors; it can be shown that up to 40° C. and 100% relative humidity:

$$P_w = 10\exp\left[19.0100 - \frac{5323.5}{T_w}\right] - 0.66(T - T_w) + \frac{0.66}{1007}(T - T_w)(1007 - P) \quad [6]$$

Thus the microprocessor can calculate a value of microwave refractivity and provide a suitable display.

I claim:

1. A terrestrial refractometer comprising:
   a gastight enclosure containing a fixed mass of a gas which at least approximates to an ideal gas, at least a part of the enclosure being movable in response to changes in the volume of the gas in accordance with changes in ambient temperature T and pressure P;

constraining means for constraining said movable part so as to maintain the gas at a constant volume;

force sensing means for providing a signal related to the force dP applied to the movable part by the constraining means;

temperature sensing means for sensing the ambient temperature T; and calculating means for calculating the difference dn from refractive index $n_o$ at standard temperature $T_o$ and pressure $P_o$ in accordance with the equation:

$$dn = (n_o - 1)\frac{dP}{P_o} \times \frac{T_o}{T}.$$

2. A terrestrial refractometer according to claim 1 further comprising means to determine the water vapour pressure of the ambient atmosphere whereby the microwave refractive index can be determined by the calculating means.

3. A terrestrial refractometer according to claim 1 in which the gastight enclosure is of substantially invariant transverse section and has a movable opposite endwall which varies linearly in position in accordance with ambient temperature and pressure.

4. A terrestrial refractometer according to claim 3 in which the constraining means comprises a helical spring and the force sensing means is arranged to sense the length of the spring.

5. The terrestrial refractometer according to claim 3 in which the constraining means and force sensing means comprise a strain gauge.

6. A method of providing a measure of the refractive index of the earth's atmosphere comprising the steps of:

exposing to ambient temperature T and pressure P a gastight enclosure containing a fixed mass of a gas which at least approximates to an ideal gas, at least a part of the enclosure being movable in response to changes in the volume of the gas;

constraining said movable part so as to maintain the gas at constant volume;

sensing the force dP required to provide the constraint; and determining the difference dn from refractive index $n_o$ at standard temperature $T_o$ and pressure $P_o$ from the equation:

$$dn = (n_o - 1)\frac{dP}{P_o} \times \frac{T_o}{T}.$$

* * * * *